(12) United States Patent
Sada

(10) Patent No.: US 9,040,455 B2
(45) Date of Patent: May 26, 2015

(54) METHOD FOR CONTROLLING PESTS

(71) Applicant: SUMITOMO CHEMICAL COMPANY, LIMITED, Tokyo (JP)

(72) Inventor: Yoshinao Sada, Tokyo (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 13/874,964

(22) Filed: May 1, 2013

(65) Prior Publication Data

US 2013/0345057 A1    Dec. 26, 2013

(30) Foreign Application Priority Data

Jun. 20, 2012 (JP) ................. 2012-138458

(51) Int. Cl.

| | | |
|---|---|---|
| A01N 43/84 | (2006.01) | |
| A01N 57/14 | (2006.01) | |
| A01N 43/54 | (2006.01) | |
| A01N 43/653 | (2006.01) | |
| A01N 33/00 | (2006.01) | |
| A01N 37/28 | (2006.01) | |
| A01N 33/22 | (2006.01) | |
| A01N 41/06 | (2006.01) | |
| A01N 25/00 | (2006.01) | |

(52) U.S. Cl.
CPC ............... *A01N 43/84* (2013.01); *A01N 43/54* (2013.01); *A01N 43/653* (2013.01); *A01N 33/00* (2013.01); *A01N 37/28* (2013.01); *A01N 33/22* (2013.01); *A01N 41/06* (2013.01); *A01N 25/00* (2013.01)

(58) Field of Classification Search
CPC .............................. A01N 43/84; A01N 57/14
USPC ............... 504/100, 128, 194, 225; 514/147
See application file for complete search history.

(56) References Cited

U.S. PATENT DOCUMENTS 5,948,819 A     9/1999 Ohtsuka et al.
2010/0317520 A1 12/2010 Ikeda et al.

FOREIGN PATENT DOCUMENTS

WO    WO 02/066471 A1    8/2002

OTHER PUBLICATIONS

Rizolex 100D label (Dec. 18, 2011); obtained from the Internet on Jun. 14, 2014 <http://ebookbrowsee.net/rizolex-100d-label-pdf-d254272334>.*
Valor label, Valent U.S.A. Corp. (2010).*
Askew, S.D. et al., "Cotton (*Gossypium hirsutum*) and weed response to flumioxazin applied preplant and postemergence directed," Weed Technology, vol. 16, pp. 184-190 (2002).*
Meister et al., "The Essential Guide for Plant Health Experts: Growing the Global Food Supply", Meisterpro Crop Protection Handbook, vol. 96, 2010, pp. 7, 216-219, 373, 383-384, 496, 563, 582, 609-613, ISBN: 1-892829-22-3. (2010).
Wood, "Compendium of Pesticide Common Names", published online: http://www.alanwood.net/pesticides/, (retrieved Jul. 17, 2014).

* cited by examiner

*Primary Examiner* — John Pak
(74) *Attorney, Agent, or Firm* — Birch, Stewart, Kolasch & Birch, LLP

(57) ABSTRACT

To provide a method which shows excellent effects in controlling pests in a field of soybean, corn or cotton.
A method for controlling weeds in a field of soybean, corn or cotton, wherein the field of soybean, corn or cotton is treated with at least one PPO-inhibiting compound selected from the group consisting of flumioxazin, sulfentrazone, saflufenacil, oxyfluorfen, fomesafen-sodium, and the compound of the formula (I):

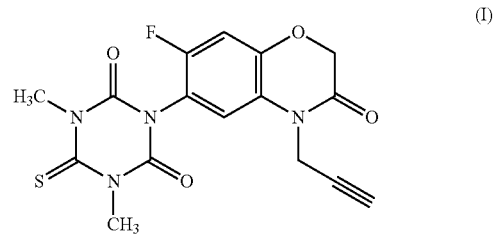

before, at or after seeding with a seed of soybean, corn or cotton treated with one or more fungicidal compounds selected from the group consisting of tolclophos-methyl, thiram, captan, carbendazim, thiophanate-methyl, and (RS)-2-methoxy-N-methyl-2-[alpha-(2,5-xylyloxy)-o-tolyl]acetamide.

4 Claims, No Drawings

METHOD FOR CONTROLLING PESTS

BACKGROUND OF THE INVENTION

1. Field of the Invention

The present invention relates to a method for controlling pests, namely, plant pathogens and/or weeds.

2. Description of the Related Art

Various compounds are known as active ingredients for fungicides. In addition, PPO-inhibiting compounds are known as active ingredients for herbicides.

DESCRIPTION OF THE RELATED ART

Patent Document

Patent Document 1: WO 02/066471
Patent Document 2: WO 95/027693

Non Patent Document

Non-Patent Document 1: Crop Protection Handbook, vol. 96 (2010)
Non-Patent Document 2: Compendium of Pesticide Common Names (http://www.alanwood.net/pesticides/)

SUMMARY OF THE INVENTION

An object of the present invention is to provide a method which shows excellent effects in controlling pests in a field of soybean, corn or cotton.

The present invention is a method for controlling pests occurring in a field by treating a field of corn, soybean or cotton with a PPO-inhibiting compound, before, at or after seeding with a seed of corn, soybean or cotton treated with a specific fungicidal compound.

The present invention is as described below.

[1] A method for controlling a weed in a field of soybean, corn or cotton, comprising applying at least one PPO-inhibiting compound selected from the group consisting of flumioxazin, sulfentrazone, saflufenacil, oxyfluorfen, fomesafen-sodium, and the compound of the formula (I):

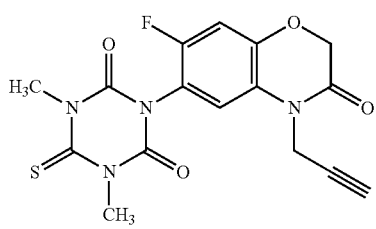

to a field before, at or after seeding with a seed of soybean, corn or cotton treated with one or more fungicidal compounds selected from the group consisting of tolclophos-methyl, thiram, captan, carbendazim, thiophanate-methyl, and (RS)-2-methoxy-N-methyl-2-[alpha-(2,5-xylyloxy)-o-tolyl]ace tamide.

[2] A method for controlling a pest in a field of soybean, corn or cotton, comprising the steps of:
treating a seed of soybean, corn or cotton with one or more fungicidal compounds selected from the group consisting of tolclophos-methyl, thiram, captan, carbendazim, thiophanate-methyl, and (RS)-2-methoxy-N-methyl-2-[alpha-(2,5-xylyloxy)-o-tolyl]ace tamide, and
treating a field before, at or after seeding with the seed of soybean, corn or cotton with one or more PPO-inhibiting compound selected from the group consisting of flumioxazin, sulfentrazone, saflufenacil, oxyfluorfen, fomesafen-sodium, and the compound of the formula (I):

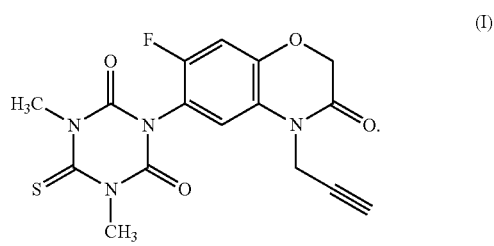 [SMILES: C#CCN1C(=O)COc2cc(F)c(-n3c(=O)n(C)c(=S)n(C)c3=O)cc21]

[3] The control method according to [1] or [2], wherein the PPO-inhibiting compound is flumioxazin.

[4] The control method according to [2], comprising the step of treating a field of soybean, corn or cotton with the PPO-inhibiting compound before seeding with a seed of soybean, corn or cotton.

[5] The control method according to [2], comprising the step of treating a field of soybean, corn or cotton with the PPO-inhibiting compound at seeding with a seed of soybean, corn or cotton.

[6] The control method according to [2], comprising the step of treating a field of soybean, corn or cotton with the PPO-inhibiting compound after seeding with a seed of soybean, corn or cotton.

[7] The control method according to [2], wherein the pest is a weed and/or a plant pathogen.

[8] The control method according to [2], wherein the pest is a weed.

According to the present invention, pests in a field of soybean, corn or cotton can be controlled.

DETAILED DESCRIPTION OF THE PREFERRED EMBODIMENTS

The method for controlling pests of the present invention comprises the steps of:
(1) treating a seed of soybean, corn or cotton with one or more fungicidal compounds selected from the group consisting of tolclophos-methyl, thiram, captan, carbendazim, thiophanate-methyl, and (RS)-2-methoxy-N-methyl-2-[alpha-(2,5-xylyloxy)-o-tolyl]ace tamide, and
(2) treating a field of soybean, corn or cotton with at least one PPO-inhibiting compound selected from the group consisting of flumioxazin, sulfentrazone, saflufenacil, oxyfluorfen, fomesafen-sodium, and the compound of the formula (I):

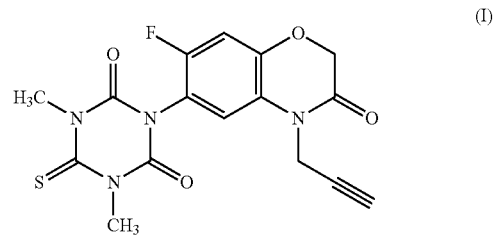 [SMILES: C#CCN1C(=O)COc2cc(F)c(-n3c(=O)n(C)c(=S)n(C)c3=O)cc21]

before, at or after seeding with the treated seed of soybean, corn or cotton.

In the present invention, the seed of soybean, corn or cotton is not limited as far as it is a variety which is generally cultivated as a crop.

Examples of a plant of such a variety include plants to which resistance to a PPO-inhibiting compound such as flumioxazin; a 4-hydroxyphenylpyruvate dioxygenase-inhibiting compound such as isoxaflutole; an acetolactate synthase (hereinafter abbreviated as ALS)-inhibiting compound such as imazethapyr or thifensulfuron methyl; a 5-enolpyruvylshikimate-3-phosphate synthase-inhibiting compound such as glyphosate; a glutamine synthase-inhibiting compound such as glufosinate; an auxin-type herbicide such as 2,4-D or dicamba; or bromoxynil has been imparted by a classical breeding method or a genetic engineering technique.

Examples of a crop to which resistance has been imparted by a classical breeding method include corn resistant to an imidazolinone type ALS-inhibiting herbicide such as imazethapyr, and this has already been commercially available under a trade name of Clearfield (registered trademark). Examples of such a crop also include STS soybean which is resistant to a sulfonylurea-type ALS-inhibiting herbicide such as thifensulfuron methyl. Similarly, examples of a plant to which resistance to an acetyl CoA carboxylase-inhibiting compound such as trione oxime-type or aryloxyphenoxypropionic acid-type herbicide has been imparted by a classical breeding method include SR corn.

Examples of a plant to which resistance has been imparted by a genetic engineering technique include corn, soybean and cotton varieties which are resistant to glyphosate, and they have already been commercially available under trade names of RoundupReady (registered trade mark), Agrisure (registered trademark) GT, Gly-Tol (registered trademark) and the like. Similarly, there are corn, soybean and cotton varieties which are resistant to glufosinate by a genetic engineering technique, and they have already been commercially available under trade names of LibertyLink (registered trademark) and the like. There are corn and soybean varieties under the trade name of Optimum (registered trademark) GAT (registered trade mark), which are resistant to both of glyphosate and an ALS-inhibiting compound. Similarly, there are soybean varieties which are resistant to an imidazolinone-type ALS-inhibiting compound by a genetic engineering technique, and they have been developed under the name of Cultivance. Similarly, there is cotton varieties which are resistant to bromoxynil by a genetic engineering technique, and this has already been commercially available under the trade name of BXN (registered trademark).

A crop such as a soybean which is resistant to dicamba can be produced by introducing a dicamba degrading enzyme such as dicamba monooxygenase isolated from *Pseudomonas maltophilia* into a plant (Behrens at al. 2007 Science 316: 1185-1188).

By introducing a gene encoding aryloxyalkanoate dioxygenase, a crop which becomes resistant to a phenoxy acid-type herbicide such as 2,4-D, MCPA, dichlorprop or mecoprop, and an aryloxyphenoxypropionic acid-type herbicide such as quizalofop, haloxyfop, fluazifop, diclofop, fenoxaprop, metamifop, cyhalofop and clodinafop can be produced (Wright et al. 2010: Proceedings of National Academy of Science. 107 (47): 20240-20245).

The crop includes, for example, a crop which has become possible to synthesize a selective toxin known in *Bacillus* genus, using a genetic engineering technique.

Examples of the toxin which is expressed in such a genetically engineered plant include an insecticidal protein derived from *Bacillus cereus* or *Bacillus popilliae*; a δ-endotoxin such as Cry1Ab, Cry1Ac, Cry1F, Cry1Fa2, Cry2Ab, Cry3A, Cry3Bb1, Cry9C, Cry34ab and Cry35ab, derived from *Bacillus thuringiensis*; an insecticidal protein such as VIP1, VIP2, VIP3 or VIP3A; an insecticidal protein derived from nematode; a toxin produced by an animal such as a scorpion toxin, a spider toxin, a bee toxin or an insect-specific neurotoxin; a filamentous fungus toxin; plant lectin; agglutinin; a protease inhibitor such as a trypsin inhibitor, a serine protease inhibitor, patatin, cystatin, and a papain inhibitor; a ribosome inactivating protein (RIP) such as lysine, corn-RIP, abrin, luffin, saporin or bryodin; a steroid metabolism enzyme such as 3-hydroxysteroid oxidase, ecdysteroid-UDP-glycosyltransferase, and cholesterol oxidase; an ecdysone inhibitor; HMG-CoA reductase; an ion channel inhibitor such as a sodium channel inhibitor or a calcium channel inhibitor; juvenile hormone esterase; a diuretic hormone receptor; stilbene synthase; bibenzyl synthase; chitinase; glucanase; and the like.

A toxin expressed by such a genetically engineered crop includes a hybrid toxin of a δ-endotoxin protein such as Cry1Ab, Cry1Ac, Cry1F, Cry1Fa2, Cry2Ab, Cry3A, Cry3Bb1, Cry9C, Cry34Ab or Cry35Ab, and an insecticidal protein such as VIP1, VIP2, VIP3 or VIP3A, and a partially deleted toxin, and a modified toxin. The hybrid toxin can be produced by a new combination of different domains of these proteins using a genetic engineering technique. As the partially deleted toxin, Cry1Ab in which a part of an amino acid sequence has been deleted is known. In the modified toxin, one or a plurality of amino acids of a natural toxin are substituted. Examples of these toxins and recombinant plants which can synthesize these toxins are described in EP-A-0374753, WO 93/07278, WO 95/34656, EP-A-0427529, EP-A-451878, WO 03/052073 and the like. The toxins contained in these recombinant plans impart resistance to *Coleoptera* vermin, *Diptera* vermin and *Lepidoptera* vermin to a plant.

In addition, a genetically engineered plant containing one or a plurality of insecticidal vermin-resistant genes and expressing one or a plurality of toxins has already been known, and some of them are commercially available. Examples of these genetically engineered plants include YieldGard (registered trademark) (corn variety expressing Cry1Ab toxin), YieldGard Rootworm (registered trademark) (corn variety expressing Cry3Bb1 toxin), YieldGard Plus (registered trademark) (corn variety expressing Cry1Ab and Cry3Bb1 toxins), Herculex I (registered trademark) (corn variety expressing phosphinothricin N-acetyltransferase (PAT) for imparting resistance to a Cry1Fa2 toxin and glufosinate), NatureGard (registered trademark), AGRISURE (registered trademark) CB Advantage (Bt11 corn borer (CB) trait), and Protecta (registered trademark).

In addition, genetically engineered cotton containing one or a plurality of insecticidal vermin-resistant genes and expressing one or a plurality of toxins have already been known, and some of them are commercially available. Examples of these genetically engineered cotton include BollGard (registered trademark) (cotton variety expressing Cry1Ac toxin), BollGard (registered trademark) II (cotton variety expressing Cry1Ac and Cry2Ab toxins), BollGard (registered trademark) III (cotton variety expressing Cry1Ac, Cry2Ab and VIP3A toxins), VipCot (registered trademark) (cotton variety expressing VIP3A and Cry1Ab toxins), WideStrike (registered trademark) (cotton variety expressing Cry1Ac and Cry1F toxins).

Examples of the plant used in the present invention also include plants to which resistance to an aphid has been imparted, such as soybeans into which a Rag1 (Resistance Aphid Gene 1) gene has been introduced.

In addition, the plant used in the present invention also includes those provided with the resistance to nematodes using a classical breeding method or genetic recombination technology. RNAi is exemplified as the genetic recombination technology providing nematode resistance.

The crop also includes a crop to which the ability to produce an anti-pathogenic substance having selective action has been imparted using a genetic engineering technique. As an example of the anti-pathogenic substance, a PR protein and the like are known (PRPs, EP-A-0392225). Such an anti-pathogenic substance and a genetically engineered plant producing the substance are described in EP-A-0392225, WO 95/33818, EP-A-0353191 and the like. Examples of the anti-pathogenic substance expressed in such a genetically engineered plant include an ion channel inhibitor such as a sodium channel inhibitor or a calcium channel inhibitor (KP1, KP4 and KP6 toxins, etc., which are produced by viruses, have been known); stilbene synthase; bibenzyl synthase; chitinase; glucanase; a PR protein; and an anti-pathogenic substance generated by microorganisms, such as a peptide antibiotic, an antibiotic having a hetero ring, or a protein factor associated with resistance to plant diseases (which is called a plant disease-resistant gene and is described in WO 03/000906).

The crop also includes a plant to which a useful character such as oil cake component modification or an amino acid content enhancing character has been imparted using a genetic engineering technique. Examples thereof include VISTIVE (registered trademark) (low linolenic soybean having a reduced linolenic content) and high-lysine (high-oil) corn (corn having an increased lysine or oil content).

Further, stack varieties are also included in which a plurality of the classical herbicide character or herbicide-resistant gene, insecticidal vermin-resistant gene, anti-pathogenic substance production gene, and a useful character such as oil cake component modification or amino acid content enhancing character are combined.

In the present invention, the fungicidal compound used in treating a seed (hereinafter, may be referred to as the fungicidal compound of the present invention) includes tolclophos-methyl, thiram, captan, carbendazim, thiophanate-methyl, and (RS)-2-methoxy-N-methyl-2-[alpha-(2,5-xylyloxy)-o-tolyl]ace tamide (hereinafter, referred to as compound 2). 2-methoxy-N-methyl-2-[alpha-(2,5-xylyloxy)-o-tolyl]acetamid e is a compound represented by the following formula:

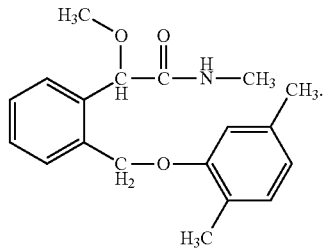 [SMILES: CNC(=O)C(OC)c1ccccc1COc1cc(C)ccc1C]

These compounds are all known compound, and compound 2 can be synthesized by the method described in WO 95/027693. Other fungicidal compounds of the present invention can be all used by purchasing a commercially available formulation or reference standard.

In the present invention, the fungicidal compound of the present invention is usually formulated by mixing with a carrier such as a solid carrier and a liquid carrier, and further adding an adjuvant for formulation such as a surfactant, as necessary. The preferable dosage form is an aqueous liquid suspension formulation.

The amount of the fungicidal compounds of the present invention is in the range of usually 0.002 to 50 g, preferably from 0.005 to 10 g, more preferably from 0.01 to 1 g, and further preferably 0.05 to 0.5 g, per 1 kg of seeds. Examples of the method of applying a seed of the plant with the fungicidal compounds of the present invention include a method of dust-coating a formulation containing the fungicidal compounds of the present invention on a seed, a method of immersing a seed in a formulation containing the fungicidal compounds of the present invention, a method of spraying a formulation containing the fungicidal compounds of the present invention on a seed, and a method of coating a seed with a carrier containing the fungicidal compounds of the present invention.

In the present invention, a field of soybean, corn or cotton is treated with at least one PPO-inhibiting compound, before, at or after seeding with a seed of soybean, corn or cotton treated with the fungicidal compound of the present invention.

The PPO-inhibiting compound is a compound that inhibits protoporphyrinogen IX oxidase (EC 1.3.3.4) located in the chlorophyll synthesis pathway in plant plasmid, and consequently kills the plant.

The PPO-inhibiting compound in the present invention includes flumioxazin, sulfentrazone, saflufenacil, oxyfluorfen, fomesafen-sodium, and a compound of the formula (I):

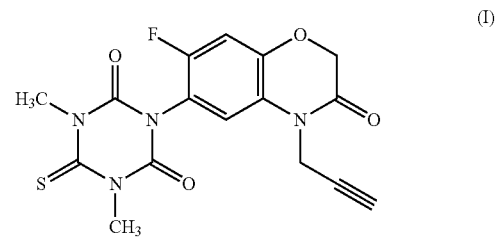 [SMILES: C#CCN1C(=O)COc2cc(F)c(-n3c(=O)n(C)c(=S)n(C)c3=O)cc21]

(hereinafter, referred to as compound 1).

These PPO-inhibiting compounds are all known compound, and compound 1 is synthesized by the method described in WO 02/066471. Other compounds can be used by purchasing a commercially available formulation or reference standard.

In the step of treating a field with a PPO-inhibiting compound, the PPO-inhibiting compound is usually formulated by mixing with a carrier such as a solid carrier and a liquid carrier, and further adding an adjuvant for formulation such as a surfactant, as necessary.

Examples of the method of treating a field with a PPO-inhibiting compound include a method of spraying the PPO-inhibiting compound on the soil in the field and a method of spraying the PPO-inhibiting compound on weeds after occurrence of weeds.

The amount of the PPO-inhibiting compound used in the step of treating a field with a PPO-inhibiting compound is usually 5 to 5000 g per 10000 $m^2$, preferably 10 to 1000 g per 10000 $m^2$, and more preferably 20 to 500 g per 10000 $m^2$. Here, in the step of treating a field with a PPO-inhibiting compound, the PPO-inhibiting compound may be mixed with an adjuvant and applied.

The seed of soybean, corn or cotton treated with the fungicidal compound of the present invention is seeded in a field by the usual method. In the method for controlling pests of the present invention, the PPO-inhibiting compound may be applied before seeding with the seed of soybean, corn or cotton, and the PPO-inhibiting compound may be applied at or after seeding with the seed of soybean, corn or cotton.

When the PPO-inhibiting compound is applied before seeding with the seed of soybean or corn, the PPO-inhibiting compound is applied 50 days before seeding to immediately before seeding, preferably 30 days before seeding to immediately before seeding, and further preferably 20 days before seeding to immediately before seeding.

When the PPO-inhibiting compound is applied after seeding with the seed of soybean or corn, the PPO-inhibiting compound is applied preferably immediately after seeding to 50 days after seeding, and more preferably immediately after seeding to 3 days after seeding. Specific application timing of applying with the PPO-inhibiting compound after seeding with the soybean seed includes, for example, the time from pre-emergence of soybean to flowering time. The time from pre-emergence of soybean to flowering time is preferably the time from pre-emergence of soybean to a stage of 6 compound leaves, and further preferably the time from pre-emergence of soybean to a stage of 3 compound leaves. Specific treatment time of applying with the PPO-inhibiting compound after seeding with the corn seed includes the time from pre-emergence of corn to 12 leaf stage, preferably the time from pre-emergence of corn to 8 leaf stage, and further preferably the time from pre-emergence of corn to 6 leaf stage. Here, the leaf age of corn is determined by the leaf collar method.

When the PPO-inhibiting compound is applied before seeding with the cotton seed, the PPO-inhibiting compound is applied 50 days before seeding to immediately before seeding, preferably 30 days before seeding to immediately before seeding, and further preferably 20 days before seeding to immediately before seeding.

When the PPO-inhibiting compound is applied after seeding with the cotton seed, the PPO-inhibiting compound is applied immediately after seeding to 70 days after seeding, and preferably 30 days after seeding to 50 days after seeding. Specific application timing of applying with the PPO-inhibiting compound after seeding with the cotton seed includes, for example, the time from pre-emergence of cotton to flowering time. Preferably, the application timing is the time from the onset of lignification of the stem base of cotton to the stage in which the lignification part is 20 cm from the base.

According to the method for controlling pests of the present invention, pests such as plant pathogens and/or weeds in a field of soybean, corn or cotton without causing phytotoxicity that is a practical problem on crops can be controlled.

The plant pathogens include the following.

*Cercospora kikuchii, icrosphaera diffusa, Diaporthe phaseolorum* var. *sojae, Septoria glycines, Cercospora sojina, Phakopsora pachyrhizi, Rhizoctonia solani, Sclerotinia sclerotiorum, Cercospora zeae-maydis, Elsinoe glycines, Ustilago maydis, Cochliobolus heterostrophus, Gloeocercospora sorghi, Cercospora gossypina, Phakopsora gossypii, Colletotrichum gossypii, Peronospora gossypina, Phyotophthora* spp., *Aspergillus* spp., *Penicillium* spp., *Fusarium* spp., *Tricoderma* spp., *Thielaviopsis* spp., *Rhizopus* spp., *Mucor* spp., *Corticium* spp., *Phoma* spp., *Diplodia* spp., *Verticillium* spp., *Puccinia* spp., *Mycosphaerella* spp., *Phytophtora* spp., *Pythium* spp., *Alternaria* spp.

Examples of the weed include the followings:

Urticaceae weeds: *Urtica urens*

Polygonaceae weeds: *Polygonum convolvulus, Polygonum lapathifolium, Polygonum pensylvanicum, Polygonum persicaria, Polygonum longisetum, Polygonum aviculare, Polygonum arenastrum, Polygonum cuspidatum, Rumex japonicus, Rumex crispus, Rumex obtusifolius, Rumex acetosa*

Portulacaceae weeds: *Portulaca oleracea*

Caryophyllaceae weeds: *Stellaria media, Cerastium holosteoides, Cerastium glomeratum, Spergula arvensis, Silene gallica*

Aizoaceae weeds: *Mollugo verticillata*

Chenopodiaceae weeds: *Chenopodium album, Chenopodium ambrosioides, Kochia scoparia, Salsola kali, Atriplex* spp.

Amaranthaceae weeds: *Amaranthus retroflexus, Amaranthus viridis, Amaranthus lividus, Amaranthus spinosus, Amaranthus hybridus, Amaranthus palmeri, Amaranthus rudis, Amaranthus patulus, Amaranthus tuberculatos, Amaranthus blitoides, Amaranthus deflexus, Amaranthus quitensis, Alternanthera philoxeroides, Alternanthera sessilis, Alternanthera tenella*

Papaveraceae weeds: *Papaver rhoeas, Argemone mexicana*

Brassicaceae weeds: *Raphanus raphanistrum, Raphanus sativus, Sinapis arvensis, Capsella bursa-pastoris, Brassica juncea, Brassica campestris, Descurainia pinnata, Rorippa islandica, Rorippa sylvestris, Thlaspi arvense, Myagrum rugosum, Lepidium virginicum, Coronopus didymus*

Capparaceae weeds: *Cleome affinis*

Fabaceae weeds: *Aeschynomene indica, Aeschynomene rudis, Sesbania exaltata, Cassia obtusifolia, Cassia occidentalis, Desmodium tortuosum, Desmodium adscendens, Trifolium repens, Pueraria lobata, vicia angustifolia, Indigofera hirsuta, Indigofera truxillensis, Vigna sinensis*

Oxalidaceae weeds: *Oxalis corniculata, Oxalis strica, Oxalis oxyptera*

Geraniaceae weeds: *Geranium carolinense, Erodium cicutarium*

Euphorbiaceae weeds: *Euphorbia helioscopia, Euphorbia maculata, Euphorbia humistrata, Euphorbia esula, Euphorbia heterophylla, Euphorbia brasiliensis, Acalypha australis, Croton glandulosus, Croton lobatus, Phyllanthus corcovadensis, Ricinus communis*

Malvaceae weeds: *Abutilon theophrasti, Sida rhombiforia, Sida cordifolia, Sida spinosa, Sida glaziovii, Sida santaremnensis, Hibiscus trionum, Anoda cristata, Malvastrum coromandelianum*

Sterculiaceae weeds: *Waltheria indica*

Violaceae weeds: *Viola arvensis, Viola tricolor*

Cucurbitaceae weeds: *Sicyos angulatus, Echinocystis lobata, Momordica charantia*

Lythraceae weeds: *Lythrum salicaria*

Apiaceae weeds: *Hydrocotyle sibthorpioides*

Sapindaceae weeds: *Cardiospermum halicacabum*

Primulaceae weeds: *Anagallis arvensis*

Asclepiadaceae weeds: *Asclepias syriaca, Ampelamus albidus*

Rubiaceae weeds: *Galium aparine, Galium spurium* var. *echinospermon, Spermacoce latifolia, Richardia brasiliensis, Borreria alata*

Convolvulaceae weeds: *Ipomoea nil, Ipomoea hederacea, Ipomoea purpurea, Ipomoea hederacea* var. *integriuscula, Ipomoea lacunosa, Ipomoea triloba, Ipomoea acuminata, Ipomoea hederifolia, Ipomoea coccinea, Ipomoea quamoclit, Ipomoea grandifolia, Ipomoea aristolochiafolia, Ipomoea cairica, Convolvulus arvensis, Calystegia hederacea, Calystegia japonica, Merremia hedeacea, Merremia aegyptia, Merremia cissoides, Jacquemontia tamnifolia*

Boraginaceae weeds: *Myosotis arvensis*

Lamiaceae weeds: *Lamium purpureum, Lamium amplexicaule, Leonotis nepetaefolia, Hyptis suaveolens, Hyptis lophanta, Leonurus sibiricus, Stachys arvensis*

Solanaceae weeds: *Datura stramonium, Solanum nigrum, Solanum americanum, Solanum ptycanthum, Solanum sarrachoides, Solanum rostratum, Solanum aculeatissimum, Solanum sisymbriifolium, Solanum carolinense, Physalis angulata, Physalis subglabrata, Nicandra physaloides*

Scrophulariaceae weeds: *Veronica hederaefolia, Veronica persica, Veronica arvensis*

Plantaginaceae weeds: *Plantago asiatica*

Asteraceae weeds: *Xanthium pensylvanicum, Xanthium occidentale, Helianthus annuus, Matricaria chamomilla, Matricaria perforata, Chrysanthemum segetum, Matricaria matricarioides, Artemisia princeps, Artemisia vulgaris, Artemisia verlotorum, Solidago altissima, Taraxacum officinale, Galinsoga ciliata, Galinsoga parviflora, Senecio vulgaris, Senecio brasiliensis, Senecio grisebachii, Conyzabonariensis, Conyza canadensis, Ambrosia artemisiaefolia, Ambrosia trifida, Bidens pilosa, Bidens frondosa, Bidens subalternans, Cirsium arvense, Cirsium vulgare, Silybum marianum, Carduus nutans, Lactuca serriola, Sonchus oleraceus, Sonchus asper, Wedelia glauca, Melampodium perfoliatum, Emilia sonchifolia, Tagetes minuta, Blainvillea latifolia, Tridax procumbens, Porophyllum ruderale, Acanthospermum australe, Acanthospermum hispidum, Cardiospermum halicacabum, Ageratum conyzoides, Eupatorium perfoliatum, Eclipta alba, Erechtites hieracifolia, Gamochaeta spicata, Gnaphalium spicatum, Jaegeria hirta, Parthenium hysterophorus, Siegesbeckia orientalis, Soliva sessilis*

Liliaceae weeds: *Allium canadense, Allium vineale*

Commelinaceae weeds: *Commelina communis, Commelina bengharensis, Commelina erecta*

Poaceae weeds: *Echinochloa crus-galli, Setaria viridis, Setaria faberi, Setaria glauca, Setaria geniculata, Digitaria ciliaris, Digitaria sanguinalis, Digitaria horizontalis, Digitaria insularis, Eleusine indica, Poa annua, Alospecurus aequalis, Alopecurus myosuroides, Avena fatua, Sorghum halepense, Sorghum vulgare, Agropyron repens, Lolium multiflorum, Loliumperenne, Lolium rigidum, Bromus secalinus, Bromus tectorum, Hordeumjubatum, Aegilops cylindrica, Phalaris arundinacea, Phalaris minor, Apera spica-venti, Panicum dichotomiflorum, Panicum texanum, Panicum maximum, Brachiaria platyphylla, Brachiaria ruziziensis, Brachiaria plantaginea, Brachiaria decumbens, Brachiaria brizantha, Brachiaria humidicola, Cenchrus echinatus, Cenchrus pauciflorus, Eriochloa villosa, Pennisetum setosum, Chloris gayana, Eragrostis pilosa, Rhynchelitrum repens, Dactyloctenium aegyptium, Ischaemum rugosum, Oryza sativa, Paspalum notatum, Paspalum maritimum, Pennisetum clandestinum, Pennisetum setosum, Rottboellia cochinchinensis*

Cyperaceae weeds: *Cyperus microiria, Cyperus iria, Cyperus odoratus, Cyperus rotundus, Cyperus esculentus, Kyllinga gracillima*

Equisetaceae weeds: *Equisetum arvense, Equisetum palustre*, and the like.

In the method for controlling pests of the present invention, one or more other pesticides can be used together or separately with the fungicidal compound of the present invention and the PPO-inhibiting compound of the present invention. Examples of other pesticide include insecticides, miticides, nematicides, fungicides, herbicides, plant growth regulators, and safeners.

Examples of the other agrochemicals include the following:

Herbicide: dicamba and a salt thereof (diglycolamine salt, dimethylammonium salt, isopropylammonium salt, potassium salt, sodium salt, choline salt), 2,4-D and a salt or ester thereof (butotyl ester, dimethylammonium salt, diolamine salt, ethylhexyl ester, isooctyl ester, isopropylammonium salt, sodium salt, triisopropanolamine salt, choline salt), 2,4-DB and a salt or ester thereof (dimethylammonium salt, isooctyl ester, choline salt), MCPA and a salt or ester thereof (dimethylammonium salt, 2-ethylhexyl ester, isooctyl ester, sodium salt, choline salt), MCPB, mecoprop and a salt or ester thereof (dimethylammonium salt, diolamine salt, ethadyl ester, 2-ethylhexyl ester, isooctyl ester, methyl ester, potassium salt, sodium salt, trolamine salt, choline salt), mecoprop-P and a salt or ester thereof (dimethylammonium salt, 2-ethylhexyl ester, isobutyl salt, potassium salt, choline salt), dichlorprop and a salt or ester thereof (butotyl ester, dimethylammonium salt, 2-ethylhexyl ester, isooctyl ester, methyl ester, potassium salt, sodium salt, choline salt), dichlorprop-P, dichlorprop-P-dimethylammonium, bromoxynil, bromoxynil-octanoate, dichlobenil, ioxynil, ioxynil-octanoate, di-allate, butylate, tri-allate, phenmedipham, chlorpropham, asulam, phenisopham, benthiocarb, molinate, esprocarb, pyributicarb, prosulfocarb, orbencarb, EPTC, dimepiperate, swep, propachlor, metazachlor, alachlor, acetochlor, metolachlor, S-metolachlor, butachlor, pretilachlor, thenylchlor, aminocyclopyrachlor, aminocyclopyrachlor-methyl, aminocyclopyrachlor-potassium, trifluralin, pendimethalin, ethalfluralin, benfluralin, prodiamine, simazine, atrazine, propazine, cyanazine, ametryn, simetryn, dimethametryn, prometryn, indaziflam, triaziflam, metribuzin, hexazinone, isoxaben, diflufenican, diuron, linuron, fluometuron, difenoxuron, methyl-daimuron, isoproturon, isouron, tebuthiuron, benzthiazuron, methabenzthiazuron, propanil, mefenacet, clomeprop, naproanilide, bromobutide, daimuron, cumyluron, diflufenzopyr, etobenzanid, bentazon, tridiphane, indanofan, amitrole, fenchlorazole, clomazone, maleic hydrazide, pyridate, chloridazon, norflurazon, bromacil, terbacil, oxaziclomefone, cinmethylin, benfuresate, cafenstrole, pyrithiobac, pyrithiobac-sodium, pyriminobac, pyriminobac-methyl, bispyribac, bispyribac-sodium, pyribenzoxim, pyrimisulfan, pyriftalid, fentrazamide, dimethenamid, dimethenamid-P, ACN, bennzobicyclon, dithiopyr, triclopyr and a salt or ester thereof (butotyl ester, triethylammonium salt), fluoroxypyr, fluoroxypyr-meptyl, thiazopyr, aminopyralid and a salt thereof (potassium salt, triisopropanolammonium salt, choline salt), clopyralid and a salt thereof (olamine salt, potassium salt, triethylammonium salt, choline salt), picloramanda salt thereof (potassium salt, triisopropanolammonium salt, choline salt), dalapon, chlorthiamid, amidosulfuron, azimsulfuron, bensulfuron, bensulfuron-methyl, chlorimuron, chlorimuron-ethyl, cyclosulfamuron, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, mesosulfuron, mesosulfuron-methyl, nicosulfuron, orthosulfamuron, oxasulfuron, primisulfuron, primisulfuron-methyl, propyrisulfuron, pyrazosulfuron, pyrazosulfuron-ethyl, rimsulfuron, sulfometuron, sulfometuron-methyl, sulfosulfuron, trifloxysulfuron-sodium, trifloxysulfuron, chlorsulfuron, cinosulfuron, ethametsulfuron, ethametsulfuron-methyl, iodosulfuron, iodosulfuron-methyl-sodium, metsulfuron, metsulfuron-methyl, prosulfuron, thifensulfuron, thifensulfuron-methyl, triasulfuron, tribenuron, tribenuron-methyl, triflusulfuron, triflusulfuron-methyl, tritosulfuron, picolinafen, beflubutamid, mesotrione, sulcotrione, tefurytrione, tembotrione, isoxachlortole, isoxaflutole, benzofenap, pyrasulfotole, pyrazolynate, pyrazoxyfen, topramezone, flupoxam, amicarbazone, bencarbazone, flucarbazone, flucarbazone-sodium, ipfencarbazone, propoxycarbazone, propoxycarbazone-sodium, thiencarbazone, thiencarbazone-methyl, cloransulam, cloransulam-methyl, diclosulam, florasulam, flumetsulam, metosulam, penoxsulam, pyroxsulam, imazamethabenz, imazamethabenz-methyl, imazamox, imazamox-ammonium, imazapic, imazapic-ammonium, imazapyr, imazapyr-ammonium, imazaquin, imazaquin-ammonium, imazethapyr, imazethapyr-ammonium, clodinafop, clodinafop-propargyl, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, propaquizafop, quizalofop, quizalofop-ethyl, quizalofop-P, quizalofop-P-ethyl, alloxydim, clethodim, sethoxydim, tepraloxydim, tralkoxydim, pinoxaden, pyroxasulfone, glyphosate, glyphosate-isopropylamine, glyphosate-trimethylsulfonium, glyphosate-ammonium, glyphosate-diammonium, glyphosate-sodium, glyphosate-potassium, glyphosate-guanidine, glufosinate, glufosinate-ammonium, glufosinate-P, glufosinate-P-sodium, bialafos, anilofos, bensulide, butamifos, paraquat, paraquat-dichloride, diquat and diquat-dibromide Plant growth regulating agents: hymexazol, paclobutrazol, uniconazole, uniconazole-P, inabenfide, prohexadione-calcium, 1-methylcyclopropene, trinexapac and gibberellins.

Safeners: benoxacor, cloquintocet, cloquintocet-mexyl, cyometrinil, cyprosulfamide, dichlormid, dicyclonon, dietholate, fenchlorazole, fenchlorazole-ethyl, fenclorim, flurazole, fluxofenim, furilazole, isoxadifen, isoxadifen-ethyl, mefenpyr, mefenpyr-diethyl, mephenate, naphthalic anhydride and oxabetrinil.

EXAMPLES

Hereinbelow, the present invention will be described by way of Examples, but the present invention is not limited to these Examples.

First, evaluation criteria for an insecticidal effect, a herbicidal effect, and phytotoxicity on crops described in the following examples are shown.

[Plant Pathogen Controlling Effect]

The evaluation of the plant pathogen controlling effect is classified into 0 to 100, in which the numeral "0" indicates no or little disease symptom by plant pathogen as comparison with the untreated crops at the time of the investigation, and the numeral "100" indicates that the disease symptom by plant pathogen is not completely or hardly observed.

[Herbicidal Effect and Phytotoxicity on Crops]

The evaluation of the herbicidal effect is classified into 0 to 100, in which the numeral "0" indicates no or little difference in the state of pre-emergence or growth of test weeds as comparison with the untreated weeds at the time of the investigation, and the numeral "100" indicates the complete death of the test plants or the complete inhibition of their pre-emergence or growth.

The evaluation of phytotoxicity on crops is shown by "no harm" when no or little phytotoxicity is found, "low" when a slight degree of phytotoxicity is found, "moderate" when a medium degree of phytotoxicity is found, or "high" when a severe degree of phytotoxicity is found.

Example 1

Pre-Plant Application in Cotton

In the combinations shown in Table 1, the plant pathogen controlling effect, herbicidal effect, and phytotoxicity on crops are confirmed by the above standards according to the following methods.

A pot is filled with soil, the weeds are planted, and then a PPO-inhibiting compound is uniformly applied on the soil surface in an agent amount of 25, 50, 100, 200, and 400 g/ha. After 15 days, cotton seeds on which the fungicidal compounds of the present invention is attached in an agent amount of 1, 10, 100 g/100 kg seeds are seeded. This pot is placed in a greenhouse. On day 15 after seeding, the plant pathogen controlling effect, herbicidal effect, and phytotoxicity on crops are examined.

TABLE 1

| Combination | Fungicidal compound | PPO-inhibiting compound |
|---|---|---|
| 1-1 | Tolclophos-methyl | Flumioxazin |
| 1-2 | Thiram | Flumioxazin |
| 1-3 | Captan | Flumioxazin |
| 1-4 | Carbendazim | Flumioxazin |
| 1-5 | Thiophanate-methyl | Flumioxazin |
| 1-6 | Compound 2 | Flumioxazin |
| 1-7 | Tolclophos-methyl | Saflufenacil |
| 1-8 | Thiram | Saflufenacil |
| 1-9 | Captan | Saflufenacil |
| 1-10 | Carbendazim | Saflufenacil |
| 1-11 | Thiophanate-methyl | Saflufenacil |
| 1-12 | Compound 2 | Saflufenacil |
| 1-13 | Tolclophos-methyl | Sulfentrazone |
| 1-14 | Thiram | Sulfentrazone |
| 1-15 | Captan | Sulfentrazone |
| 1-16 | Carbendazim | Sulfentrazone |
| 1-17 | Thiophanate-methyl | Sulfentrazone |
| 1-18 | Compound 2 | Sulfentrazone |
| 1-19 | Tolclophos-methyl | Oxyfluorfen |
| 1-20 | Thiram | Oxyfluorfen |
| 1-21 | Captan | Oxyfluorfen |
| 1-22 | Carbendazim | Oxyfluorfen |
| 1-23 | Thiophanate-methyl | Oxyfluorfen |
| 1-24 | Compound 2 | Oxyfluorfen |
| 1-25 | Tolclophos-methyl | Fomesafen-sodium |
| 1-26 | Thiram | Fomesafen-sodium |
| 1-27 | Captan | Fomesafen-sodium |
| 1-28 | Carbendazim | Fomesafen-sodium |
| 1-29 | Thiophanate-methyl | Fomesafen-sodium |
| 1-30 | Compound 2 | Fomesafen-sodium |
| 1-31 | Tolclophos-methyl | Compound 1 |
| 1-32 | Thiram | Compound 1 |
| 1-33 | Captan | Compound 1 |
| 1-34 | Carbendazim | Compound 1 |
| 1-35 | Thiophanate-methyl | Compound 1 |
| 1-36 | Compound 2 | Compound 1 |

Example 2

Post-Directed Application in Cotton

In the combinations shown in Table 2, the plant pathogen controlling effect, herbicidal effect, and phytotoxicity on crops are confirmed by the above standards according to the following methods.

The fungicidal compounds of the present invention is attached on cotton seeds in an agent amount of 1, 10, 100 g/100 kg seeds. Next, the seeds are seeded in a farm field. On day 30 after seeding, a PPO-inhibiting compound is applied as a post-directed application in an agent amount of 25, 50, 100, 200, and 400 g/ha, in the state that the main stem of cotton is lignified in 15 cm from the ground. On day 28 after treatment, the plant pathogen controlling effect, herbicidal effect, and phytotoxicity on crops are examined.

TABLE 2

| Combination | Fungicidal compound | PPO-inhibiting compound |
|---|---|---|
| 2-1 | Tolclophos-methyl | Flumioxazin |
| 2-2 | Thiram | Flumioxazin |
| 2-3 | Captan | Flumioxazin |
| 2-4 | Carbendazim | Flumioxazin |
| 2-5 | Thiophanate-methyl | Flumioxazin |
| 2-6 | Compound 2 | Flumioxazin |
| 2-7 | Tolclophos-methyl | Saflufenacil |
| 2-8 | Thiram | Saflufenacil |
| 2-9 | Captan | Saflufenacil |
| 2-10 | Carbendazim | Saflufenacil |
| 2-11 | Thiophanate-methyl | Saflufenacil |
| 2-12 | Compound 2 | Saflufenacil |
| 2-13 | Tolclophos-methyl | Sulfentrazone |
| 2-14 | Thiram | Sulfentrazone |
| 2-15 | Captan | Sulfentrazone |
| 2-16 | Carbendazim | Sulfentrazone |
| 2-17 | Thiophanate-methyl | Sulfentrazone |
| 2-18 | Compound 2 | Sulfentrazone |
| 2-19 | Tolclophos-methyl | Oxyfluorfen |
| 2-20 | Thiram | Oxyfluorfen |
| 2-21 | Captan | Oxyfluorfen |
| 2-22 | Carbendazim | Oxyfluorfen |
| 2-23 | Thiophanate-methyl | Oxyfluorfen |
| 2-24 | Compound 2 | Oxyfluorfen |
| 2-25 | Tolclophos-methyl | Fomesafen-sodium |
| 2-26 | Thiram | Fomesafen-sodium |
| 2-27 | Captan | Fomesafen-sodium |
| 2-28 | Carbendazim | Fomesafen-sodium |
| 2-29 | Thiophanate-methyl | Fomesafen-sodium |
| 2-30 | Compound 2 | Fomesafen-sodium |
| 2-31 | Tolclophos-methyl | Compound 1 |
| 2-32 | Thiram | Compound 1 |
| 2-33 | Captan | Compound 1 |
| 2-34 | Carbendazim | Compound 1 |
| 2-35 | Thiophanate-methyl | Compound 1 |
| 2-36 | Compound 2 | Compound 1 |

Example 3

Pre-Plant Application in Soybean

In the combinations shown in Table 3, the plant pathogen controlling effect, herbicidal effect, and phytotoxicity on crops are confirmed by the above standards according to the following methods.

A pot is filled with soil, and the weeds are planted, then a PPO-inhibiting compound is uniformly applied on the soil surface in an agent amount of 25, 50, 100, 200, and 400 g/ha. After 7 days, soybean seeds on which the fungicidal compounds of the present invention is attached in an agent amount of 1, 10, 100 g/100 kg seeds are seeded. This pot is placed in a greenhouse. On day 15 after seeding, the plant pathogen controlling effect, herbicidal effect, and phytotoxicity on crops are examined.

TABLE 3

| Combination | Fungicidal compound | PPO-inhibiting compound |
|---|---|---|
| 3-1 | Tolclophos-methyl | Flumioxazin |
| 3-2 | Thiram | Flumioxazin |
| 3-3 | Captan | Flumioxazin |
| 3-4 | Carbendazim | Flumioxazin |
| 3-5 | Thiophanate-methyl | Flumioxazin |
| 3-6 | Compound 2 | Flumioxazin |
| 3-7 | Tolclophos-methyl | Saflufenacil |
| 3-8 | Thiram | Saflufenacil |
| 3-9 | Captan | Saflufenacil |
| 3-10 | Carbendazim | Saflufenacil |
| 3-11 | Thiophanate-methyl | Saflufenacil |
| 3-12 | Compound 2 | Saflufenacil |
| 3-13 | Tolclophos-methyl | Sulfentrazone |
| 3-14 | Thiram | Sulfentrazone |
| 3-15 | Captan | Sulfentrazone |
| 3-16 | Carbendazim | Sulfentrazone |
| 3-17 | Thiophanate-methyl | Sulfentrazone |
| 3-18 | Compound 2 | Sulfentrazone |
| 3-19 | Tolclophos-methyl | Oxyfluorfen |
| 3-20 | Thiram | Oxyfluorfen |
| 3-21 | Captan | Oxyfluorfen |
| 3-22 | Carbendazim | Oxyfluorfen |
| 3-23 | Thiophanate-methyl | Oxyfluorfen |
| 3-24 | Compound 2 | Oxyfluorfen |
| 3-25 | Tolclophos-methyl | Fomesafen-sodium |
| 3-26 | Thiram | Fomesafen-sodium |
| 3-27 | Captan | Fomesafen-sodium |
| 3-28 | Carbendazim | Fomesafen-sodium |
| 3-29 | Thiophanate-methyl | Fomesafen-sodium |
| 3-30 | Compound 2 | Fomesafen-sodium |
| 3-31 | Tolclophos-methyl | Compound 1 |
| 3-32 | Thiram | Compound 1 |
| 3-33 | Captan | Compound 1 |
| 3-34 | Carbendazim | Compound 1 |
| 3-35 | Thiophanate-methyl | Compound 1 |
| 3-36 | Compound 2 | Compound 1 |

Example 4

Preemergence Application in Soybean

In the combinations shown in Table 4, the plant pathogen controlling effect, herbicidal effect, and phytotoxicity on crops are confirmed by the above standards according to the following methods.

The fungicidal compounds of the present invention is attached on soybean seeds in an agent amount of 1, 10, 100 g/100 kg seeds. Next, a pot is filled with soil, and the seeds and the seeds of the weeds are seeded. On the day of the seeding, a PPO-inhibiting compound is uniformly applied on the soil surface in an agent amount of 25, 50, 100, 200, and 400 g/ha. This pot is placed in a greenhouse. On day 15 after seeding, the plant pathogen controlling effect, herbicidal effect, and phytotoxicity on crops are examined.

TABLE 4

| Combination | Fungicidal compound | PPO-inhibiting compound |
|---|---|---|
| 4-1 | Tolclophos-methyl | Flumioxazin |
| 4-2 | Thiram | Flumioxazin |
| 4-3 | Captan | Flumioxazin |
| 4-4 | Carbendazim | Flumioxazin |
| 4-5 | Thiophanate-methyl | Flumioxazin |
| 4-6 | Compound 2 | Flumioxazin |
| 4-7 | Tolclophos-methyl | Saflufenacil |
| 4-8 | Thiram | Saflufenacil |
| 4-9 | Captan | Saflufenacil |
| 4-10 | Carbendazim | Saflufenacil |
| 4-11 | Thiophanate-methyl | Saflufenacil |
| 4-12 | Compound 2 | Saflufenacil |
| 4-13 | Tolclophos-methyl | Sulfentrazone |
| 4-14 | Thiram | Sulfentrazone |
| 4-15 | Captan | Sulfentrazone |
| 4-16 | Carbendazim | Sulfentrazone |
| 4-17 | Thiophanate-methyl | Sulfentrazone |
| 4-18 | Compound 2 | Sulfentrazone |
| 4-19 | Tolclophos-methyl | Oxyfluorfen |
| 4-20 | Thiram | Oxyfluorfen |

TABLE 4-continued

| Combination | Fungicidal compound | PPO-inhibiting compound |
|---|---|---|
| 4-21 | Captan | Oxyfluorfen |
| 4-22 | Carbendazim | Oxyfluorfen |
| 4-23 | Thiophanate-methyl | Oxyfluorfen |
| 4-24 | Compound 2 | Oxyfluorfen |
| 4-25 | Tolclophos-methyl | Fomesafen-sodium |
| 4-26 | Thiram | Fomesafen-sodium |
| 4-27 | Captan | Fomesafen-sodium |
| 4-28 | Carbendazim | Fomesafen-sodium |
| 4-29 | Thiophanate-methyl | Fomesafen-sodium |
| 4-30 | Compound 2 | Fomesafen-sodium |
| 4-31 | Tolclophos-methyl | Compound 1 |
| 4-32 | Thiram | Compound 1 |
| 4-33 | Captan | Compound 1 |
| 4-34 | Carbendazim | Compound 1 |
| 4-35 | Thiophanate-methyl | Compound 1 |
| 4-36 | Compound 2 | Compound 1 |

Example 5

Preemergence Application in Corn

In the combinations shown in Table 5, the plant pathogen controlling effect, herbicidal effect, and phytotoxicity on crops are confirmed by the above standards according to the following methods.

The fungicidal compounds of the present invention is attached on corn seeds in an agent amount of 1, 10, 100 g/100 kg seeds. Next, a pot is filled with soil, and the seeds and the seeds of the weeds are seeded. On the day of the seeding, a PPO-inhibiting compound is uniformly applied on the soil surface in an agent amount of 25, 50, 100, 200, and 400 g/ha. This pot is placed in a greenhouse. On day 15 after seeding, the plant pathogen controlling effect, herbicidal effect, and phytotoxicity on crops are examined.

TABLE 5

| Combination | Fungicidal compound | PPO-inhibiting compound |
|---|---|---|
| 5-1 | Tolclophos-methyl | Flumioxazin |
| 5-2 | Thiram | Flumioxazin |
| 5-3 | Captan | Flumioxazin |
| 5-4 | Carbendazim | Flumioxazin |
| 5-5 | Thiophanate-methyl | Flumioxazin |
| 5-6 | Compound 2 | Flumioxazin |
| 5-7 | Tolclophos-methyl | Saflufenacil |
| 5-8 | Thiram | Saflufenacil |
| 5-9 | Captan | Saflufenacil |
| 5-10 | Carbendazim | Saflufenacil |
| 5-11 | Thiophanate-methyl | Saflufenacil |
| 5-12 | Compound 2 | Saflufenacil |
| 5-13 | Tolclophos-methyl | Sulfentrazone |
| 5-14 | Thiram | Sulfentrazone |
| 5-15 | Captan | Sulfentrazone |
| 5-16 | Carbendazim | Sulfentrazone |
| 5-17 | Thiophanate-methyl | Sulfentrazone |
| 5-18 | Compound 2 | Sulfentrazone |
| 5-19 | Tolclophos-methyl | Oxyfluorfen |
| 5-20 | Thiram | Oxyfluorfen |
| 5-21 | Captan | Oxyfluorfen |
| 5-22 | Carbendazim | Oxyfluorfen |
| 5-23 | Thiophanate-methyl | Oxyfluorfen |
| 5-24 | Compound 2 | Oxyfluorfen |
| 5-25 | Tolclophos-methyl | Fomesafen-sodium |
| 5-26 | Thiram | Fomesafen-sodium |
| 5-27 | Captan | Fomesafen-sodium |
| 5-28 | Carbendazim | Fomesafen-sodium |
| 5-29 | Thiophanate-methyl | Fomesafen-sodium |
| 5-30 | Compound 2 | Fomesafen-sodium |

TABLE 5-continued

| Combination | Fungicidal compound | PPO-inhibiting compound |
|---|---|---|
| 5-31 | Tolclophos-methyl | Compound 1 |
| 5-32 | Thiram | Compound 1 |
| 5-33 | Captan | Compound 1 |
| 5-34 | Carbendazim | Compound 1 |
| 5-35 | Thiophanate-methyl | Compound 1 |
| 5-36 | Compound 2 | Compound 1 |

Example 6

Pre-Plant Application in Corn

In the combinations shown in Table 6, the plant pathogen controlling effect, herbicidal effect, and phytotoxicity on crops are confirmed by the above standards according to the following methods.

A pot is filled with soil, and the weeds are planted, then a PPO-inhibiting compound is uniformly applied on the soil surface in an agent amount of 25, 50, 100, 200, and 400 g/ha. After 7 days, corn seeds on which the fungicidal compounds of the present invention is attached in an agent amount of 1, 10, 100 g/100 kg seeds are seeded. This pot is placed in a greenhouse. On day 15 after seeding, the plant pathogen controlling effect, herbicidal effect, and phytotoxicity on crops are examined.

TABLE 6

| Combination | Fungicidal compound | PPO-inhibiting compound |
|---|---|---|
| 6-1 | Tolclophos-methyl | Flumioxazin |
| 6-2 | Thiram | Flumioxazin |
| 6-3 | Captan | Flumioxazin |
| 6-4 | Carbendazim | Flumioxazin |
| 6-5 | Thiophanate-methyl | Flumioxazin |
| 6-6 | Compound 2 | Flumioxazin |
| 6-7 | Tolclophos-methyl | Saflufenacil |
| 6-8 | Thiram | Saflufenacil |
| 6-9 | Captan | Saflufenacil |
| 6-10 | Carbendazim | Saflufenacil |
| 6-11 | Thiophanate-methyl | Saflufenacil |
| 6-12 | Compound 2 | Saflufenacil |
| 6-13 | Tolclophos-methyl | Sulfentrazone |
| 6-14 | Thiram | Sulfentrazone |
| 6-15 | Captan | Sulfentrazone |
| 6-16 | Carbendazim | Sulfentrazone |
| 6-17 | Thiophanate-methyl | Sulfentrazone |
| 6-18 | Compound 2 | Sulfentrazone |
| 6-19 | Tolclophos-methyl | Oxyfluorfen |
| 6-20 | Thiram | Oxyfluorfen |
| 6-21 | Captan | Oxyfluorfen |
| 6-22 | Carbendazim | Oxyfluorfen |
| 6-23 | Thiophanate-methyl | Oxyfluorfen |
| 6-24 | Compound 2 | Oxyfluorfen |
| 6-25 | Tolclophos-methyl | Fomesafen-sodium |
| 6-26 | Thiram | Fomesafen-sodium |
| 6-27 | Captan | Fomesafen-sodium |
| 6-28 | Carbendazim | Fomesafen-sodium |
| 6-29 | Thiophanate-methyl | Fomesafen-sodium |
| 6-30 | Compound 2 | Fomesafen-sodium |
| 6-31 | Tolclophos-methyl | Compound 1 |
| 6-32 | Thiram | Compound 1 |
| 6-33 | Captan | Compound 1 |
| 6-34 | Carbendazim | Compound 1 |
| 6-35 | Thiophanate-methyl | Compound 1 |
| 6-36 | Compound 2 | Compound 1 |

According to the method for controlling pests of the present invention, pests in a field of soybean, corn or cotton can be efficiently controlled.

What is claimed is:

1. A method for controlling a weed in a field of soybean, corn or cotton, comprising applying flumioxazin to a field before, at or after seeding with a seed of soybean, corn or cotton treated with tolclophos-methyl.

2. The control method according to claim 1, wherein the flumioxazin is applied to the field before seeding with the seed of soybean, corn or cotton.

3. The control method according to claim 1, wherein the flumioxazin is applied to the field at seeding with the seed of soybean, corn or cotton.

4. The control method according to claim 1, wherein the flumioxazin is applied to the field after seeding with the seed of soybean, corn or cotton.

\* \* \* \* \*